April 26, 1966 R. G. JELLY Plant Pat. 2,623
ROSE PLANT
Filed Jan. 21, 1965
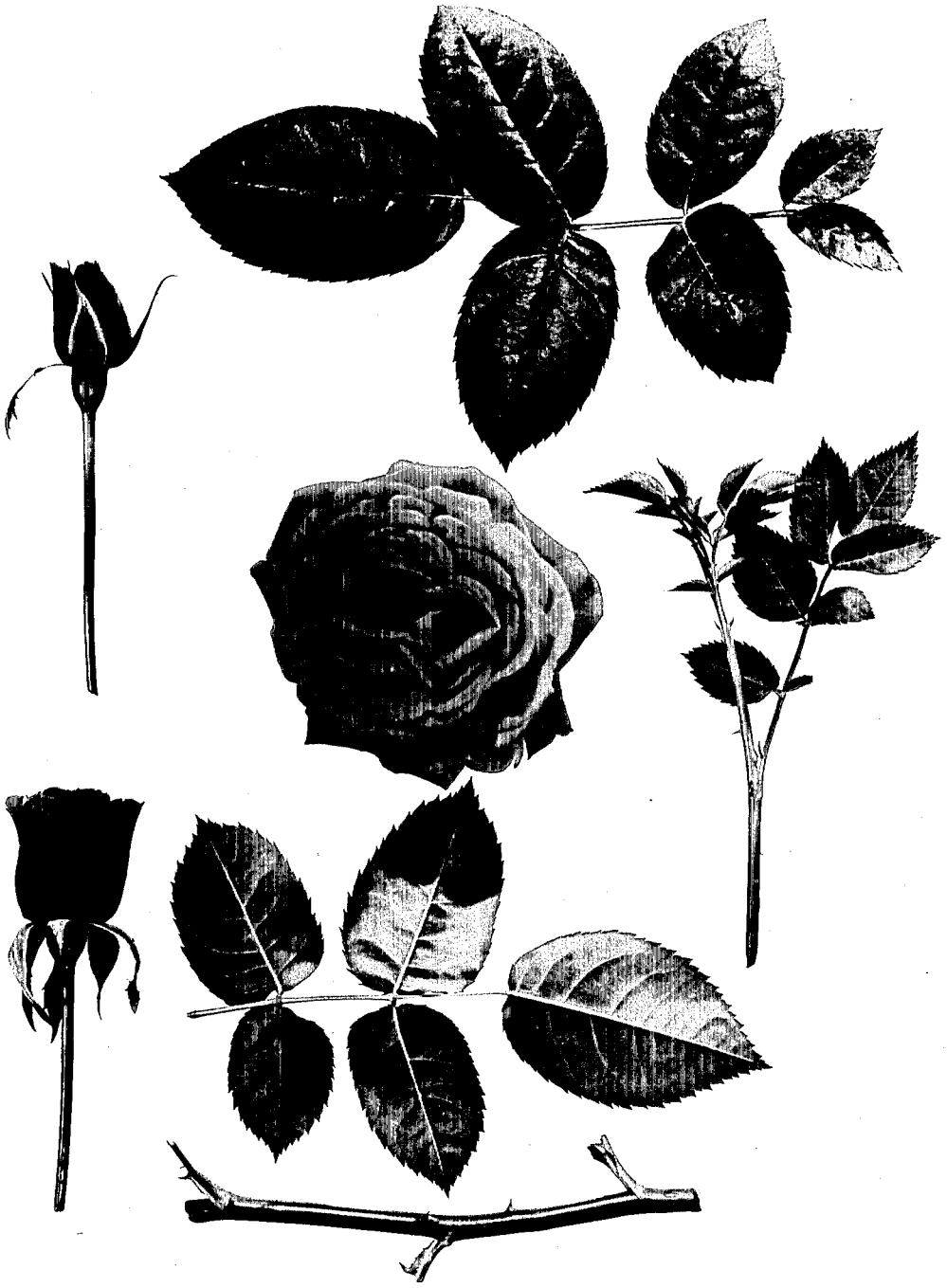
Inventor
Robert G. Jelly
By: Robb & Robb
Attorneys.

United States Patent Office

Plant Pat. 2,623
Patented Apr. 26, 1966

2,623
ROSE PLANT

Robert G. Jelly, Richmond, Ind., assignor to E. G. Hill Co., Inc., Richmond, Ind., a corporation of Indiana Filed Jan. 21, 1965, Ser. No. 427,195
1 Claim. (Cl. Plt.—29)

The present invention relates to a new and distinct variety of rose plant of the floribunda class, which was originated by me by crossing the variety "Yuletide" (Plant Patent No. 1,391) with an unnamed, unpatented and undisseminated seedling of "Garnette" (unpatented).

The primary objective of this breedling was to produce a new rose variety having an improved flower stem length in the "Garnette" line, while still maintaining the fine vase life inherent in the "Garnette" variety and its progeny. This objective was fully achieved along with other desirable improvements, as evidenced by the following unique combination of characteristics which are outstanding in the new variety and which distinguish it from its parents, as well as from all other varieties of which I am aware:

(1) An upright habit of growth;
(2) Long flower stems;
(3) Excellent flower substance and versatile utility for corsages and for table and hospital arrangements and the like; and
(4) A distinctive and attractive Dark Red flower color.

In comparison with its seed parent "Yuletide," the new variety is a floribunda instead of a Hybrid Tea as is this parent.

As compared with the unnamed pollen parent, the flower stem length of the new variety is greater and more desirable than that of this parent, and the bloom is somewhat larger, while still maintaining the excellent texture and vase life of this parent.

Considering the growth habit and flower color of the new variety, it is not similiar to any floribunda variety currently grown commercially in greenhouses. Its growth and flower bud size somewhat resembles "Stoplite" (Plant Patent No. 1,315), but it is not similar in other respects, such as flower form and color.

Asexual reproduction of the new variety by grafting, as performed at Richmond, Indiana, and also by budding, as performed at Livermore, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert S. Wilson's Horticultural Colour Chart (hereinafter abbreviated as (W)), and Nickerson Color Fan (hereinafter abbreviated as (N)), as indicated, except where general color terms of ordinary dictionary significance are obvious:

Type: Seedling; greenhouse; for cut flowers.
Class: Floribunda.
Breeding: Seedling.
*Seed parent.*—"Yuletide."
*Pollen parent.*—An unnamed seedling of "Garnette."
Propagation: Holds its distinguishing characteristics through succeeding propagations by both grafting and budding.

*Flower*

Locality where grown and where following observations were made:
Richmond, Indiana.
Flowers borne: Generally 1 to 3 but sometimes several to stem (usually disbudded commercially to a single flower); in irregular clusters; on moderately strong stems of medium length.
Quantity of bloom: Free, in greenhouse.
Continuity: Continuous, in greenhouse.
Fragrance: From none to slight, in greenhouse.

Bud:

*Peduncle.*—Medium length; medium diameter; very erect; medium strength. Bark.—Varies from Strong Yellow Green, Plate 2.5GY6/8 (N) to Moderate Yellow Green, Plate 2.5GY5/5 (N). Thorns.—None. Prickles.—None. Hairs.—None.
*Before calyx breaks.*—Size—Medium small. Form—short; pointed; with a conspicuous neck; with foliaceous appendages on the surface of the bud; with slender, much-cut foliaceous parts extending beyond the tip of the bud equal to from ½ to ¾ or more of its length. Color—Shaded from Strong Yellow Green, Plate 5GY6/8 (N), to Moderate Yellow-Green, Plate 5GY5/6 (N).
*As calyx breaks.*—Color—Outside petals shaded from Indian Lake, Plate 826 (W) to Dark Red, Plate 2.5R3/7 (N).
*As first petal opens.*—Size—medium small. Form—short pointed. Color—Outside—Shaded from Indian Lake, Plate 826 (W) at base to Cardinal Red, Plate 822/1 (W) at petal edge. Inside shaded from Chrysanthemum Crimson, Plate 824 (W) at base to Cardinal Red, Plate 822/1 (W), with both colors appearing somewhat more brilliant than chart colors due to velvety texture.
*Opening.*—Opens up well in greenhouse; bud size slightly decreases during periods of prolonged hot weather.

Bloom:

*Size (when fully open).*—From small to medium; from 2½ inches to 3¼ inches.
*Petalage.*—Double (more petals, but the stamens not hidden); from 30 to 38 petals when open for three days on plant; arranged regularly.
*Form.*—Globular at first, but becoming flat; petals being at first very tightly rolled inward, but becoming tightly rolled outward at maturity.

Petals:

*Texture.*—Moderately thick. *Appearance.*—Inside—velvety. Outside—satiny.
*Shape.*—Outer—from round to oval, with apex mucronate, and with from one to several notches. Intermediate—from round to oval, with apex mucronate, and with one slight notch. Inner—oval, with apex mucronate, and with one to several notches.

This description of a newly opened flower was made from a rose grown in a greenhouse during the month of December at Richmond, Indiana:

*Color.*—Outer petal—outside surface—shaded from Rose Red, Plate 724 (W) to slightly darker than Rose Red, Plate 724 (W), with base of Mimosa Yellow, Plate 602/3 (W); inside surface—shaded from Cardinal Red, Plate 822/2 (W) to slightly darker and brighter than Cardinal Red, Plate 822

(W), with base of Mimosa Yellow, Plate 602/3 (W). Intermediate petal—outside surface—shaded from Rose Red, Plate 724 (W) to darker than Rose Red, Plate 724 (W), with base of Mimosa Yellow, Plate 602/3; inside surface—shaded from Cardinal Red, Plate 822/2 (W) to slightly darker and brighter than Cardinal Red, Plate 822 (W), with base of Mimosa Yellow, Plate 602/3 (W). Inner petal—outside surface—shaded from Rose Red, Plate 724 (W) to darker than Rose Red, Plate 724 (W), with base of Mimosa Yellow, Plate 602/3 (W); inside surface—shaded from Cardinal Red, Plate 822/2 (W) to several shades darker and brighter than Cardinal Red, Plate 822 (W), with base of Mimosa Yellow, Plate 602/3 (W).

This description was made from a rose that was open for three days in a greenhouse during the month of December at Richmond, Indiana:

*Color.*—Outer petal—outside surface—shaded from Rose Red, Plate 724/1 (W) at base to slightly darker than Rose Red, Plate 724 (W), with base of Primrose Yellow, Plate 601/3 (W); inside surface—slightly darker than but nearest to Cardinal Red, Plate 822/2 (W), with base of Primrose Yellow, Plate 601 (W). Intermediate petal—outside surface—Rose Red, Plate 724 (W), with base of Primrose Yellow, Plate 601/3 (W); inside surface—between Rose Red, Plate 724 (W) and Cardinal Red, Plate 822/2 (W), with base of Primrose Yellow, Plate 601/3 (W). Inner petal—outside surface—Rose Red, Plate 724/1 (W), with base of Primrose Yellow, Plate 601/3 (W); inside surface—shaded from Rose Red, Plate 724 (W) to Cardinal Red, Plate 822/3 (W), with base of Primrose Yellow, Plate 601/3.

*General color effect.*—Newly opened flower—shaded from Cardinal Red, Plate 822/3 (W) to several shades darker and brighter than Cardinal Red, Plate 822 (W). 3-days open—shaded from Rose Red, Plate 724 (W) to Cardinal Red, Plate 822/3 (W).

*Behavior.*—Petals persist in greenhouse; fade slightly faster during hot, dry weather; fading to Rose Red, Plate 724 (W).

*Flower longevity.*—Cut flowers grown in greenhouse and left at living room temperatures—7 days in November.

*Plant*

Foliage:

*Leaves.*—Compound of 3 to 7, but generally 5, leaflets; normal abundance; medium size; moderately thin.

*Leaflets.*—Shape—from oval to slightly elliptical. Apex—cuspidate. Base—obtuse, with variations to oblique. Margin—serrate.

*Color.*—Mature—upper surface—varies from Ivy Green, Plate 0001060/3 (W) to Ivy Green, Plate 0001060/2 (W); under surface—varies from Leek Green, Plate 000858 (W) to a shade slightly lighter and greener. Young—upper surface Parsely Green, Plate 00962/1 (W), with lighter shading and venation to Moderate Yellow Green, Plate 2.5GY5/5 (N); under surface—Lavender Green, Plate 000761 (W), with suffusions of Moderate Reddish Brown, Plate 7.5R3/6 (N), and venation as light as Strong Greenish Yellow, Plate 7.5Y7/9 (N).

*Rachis (the supporting stem of the compound leaf).*—From light to medium. Upper side—prickly, with prickles fine and almost hairy; under side—with very small and fine thorns.

*Stipules.*—Moderately short; narrow; with short points turning out at an angle of less than 45°.

Growth (in greenhouse):

*Habit.*—Upright; much-branched.

*Growth.*—Moderately free.

*Canes.*—Medium diameter.

*Main stems.*—Color—varies from Spinach Green, Plate 0960/3 (W), to Spinach Green, Plate 0960/2 (W), with streaks of mainly moderate Yellowish Brown, Plate 10YR4/4 (N) as the plants age. Thorns—several; short; from straight to slightly hooked downward; with short, narrow base. Color—moderate Yellowish Brown, Plate 10YR4/4 (N). Prickles—few toward base of some canes, which varies with age of main canes. Color—from moderate Brown, Plate 7.5YR4/5 to as dark as Moderate Brown, Plate 5YR3/3 (N). Hairs—none.

*Branches.*—Color—varies from Spinach Green, Plate 0960/1 (W) to Spinach Green, Plate 0960 (W). Thorns—from few to several; from straight to slightly hooked downward; with narrow base. Color—varies from slightly lighter than Strong Yellowish Brown, Plate 7.5YR5/7 (N) to slightly darker than Strong Yellowish Brown, Plate 7.5YR5/7 (N). Prickles—a few occasionally at lower portion of cane. Color—Erythrite Red, Plate 0027 (W). Hairs—none.

*New shoots.*—Color—Erthyrite Red, Plate 0027 (W). Thorns—several; some short and some straight; with short, narrow base. Color—Moderate Reddish Brown, Plate 7.5R3/6 (N). Prickles—none. Hairs—none.

*Reproductive organs*

Stamens: Medium number, arranged regularly about pistils; tucked in calyx.

Filaments: Short; most with anthers.

*Color.*—Indian Lake, Plate 826/2 (W), with base of Naples Yellow, Plate 403/1 (W).

Anthers: Small; open at various times.

*Color.*—Shaded from Naples Yellow, Plate 403 (W) at center to Strong Orange Yellow, Plate 7.5YR7/11 (N), Pollen: Moderate quantity.

*Color.*—Strong Orange, Plate 5YR6/11 (N).

Pistils: Medium number.

Styles: Uneven; short; thin; bunched.

*Color.*—Rose Red, Plate 724 (W), shaded to Naples Yellow, Plate 403/2 (W) at base.

Stigma: Color—Lemon Yellow, Plate 4/2 (W).

Ovaries: A few protruding from calyx.

Hips: Short; ovoid; with a conspicuous neck; from oval to rounded; smooth; walls thin and fleshy.

*Color.*—Fern Green, Plate 086/2 (W).

Sepals: None observed; usually removed during hydridizing process.

Seeds: Many; medium size.

I claim:

A new and distinct variety of rose plant of the floribunda class, substantially as herein shown and described, characterized particularly as to novelty by the unique combination of an upright habit of growth, long flower stems, excellent flower substance and versatile utility for corsages and for table and hospital arrangements and the like; and a distinctive and attractive Dark Red flower color.

No references cited.

ANTONIO F. GUIDA, *Acting Primary Examiner.*